(12) United States Patent
Baley et al.

(10) Patent No.: US 7,425,718 B1
(45) Date of Patent: *Sep. 16, 2008

(54) LIGHTING SYSTEM, POINT SOURCE LIGHTS THEREFOR AND METHODS OF MAKING THE SAME

(76) Inventors: David Baley, deceased, late of Springfield MO (US); by Nancy Baley, legal representative, 3951 S. Mentor # 32, Springfield, MO (US) 65804; Richard L. Marsh, 4116 E. Latoka St., Springfield, MO (US) 65809

( * ) Notice: Subject to any disclaimer, the term of this patent is extended or adjusted under 35 U.S.C. 154(b) by 0 days.

This patent is subject to a terminal disclaimer.

(21) Appl. No.: 11/899,658

(22) Filed: Sep. 7, 2007

Related U.S. Application Data

(63) Continuation of application No. 11/205,683, filed on Aug. 17, 2005, now Pat. No. 7,291,852.

(51) Int. Cl.
*G01N 21/33* (2006.01)
*G01N 21/69* (2006.01)
*B63B 45/00* (2006.01)

(52) U.S. Cl. .............................. 250/504 R; 250/461.1; 250/365; 362/184; 362/191; 362/800; 362/555

(58) Field of Classification Search ............ 250/504 R, 250/461.1, 365; 362/184, 191, 800, 555
See application file for complete search history.

(56) References Cited

U.S. PATENT DOCUMENTS

| | | | |
|---|---|---|---|
| D299,550 S | 1/1989 | Payne | |
| 4,947,293 A | 8/1990 | Johnson et al. | |
| 4,954,931 A | 9/1990 | Hassler, Jr. | |
| 5,495,401 A | 2/1996 | Evans | |
| 6,174,078 B1 | 1/2001 | Ohm et al. | |
| 6,474,851 B1* | 11/2002 | Baley | 362/477 |
| 6,554,444 B2 | 4/2003 | Shimada et al. | |
| 7,018,081 B2* | 3/2006 | Hopkins | 362/477 |
| 7,291,852 B1* | 11/2007 | Matlack et al. | 250/504 R |

OTHER PUBLICATIONS

LED Ultraviolet Headlamps, Blacklight World P.O. Box 26, Cub Run, KY, 42729; www.blacklightworld.com.
Scorpion Hunter, Erin Sheffo, 3912 Nantasket St., Pittsburgh, PA 15207; www.scorpionhunting.com.

* cited by examiner

*Primary Examiner*—Nikita Wells
(74) *Attorney, Agent, or Firm*—Richard L. Marsh

(57) ABSTRACT

A lighting system comprising at least one lighting assembly, the lighting assembly comprising at least one ultraviolet light source, means for separately controlling ultraviolet light source and a mounting base, the mounting base carrying the ultraviolet light source with the means for separately controlling disposed remote therefrom, lighting assemblies of the lighting system mounted upon a portion of the side of a boat wherein the ultraviolet light source comprises an array of point lights.

20 Claims, 4 Drawing Sheets

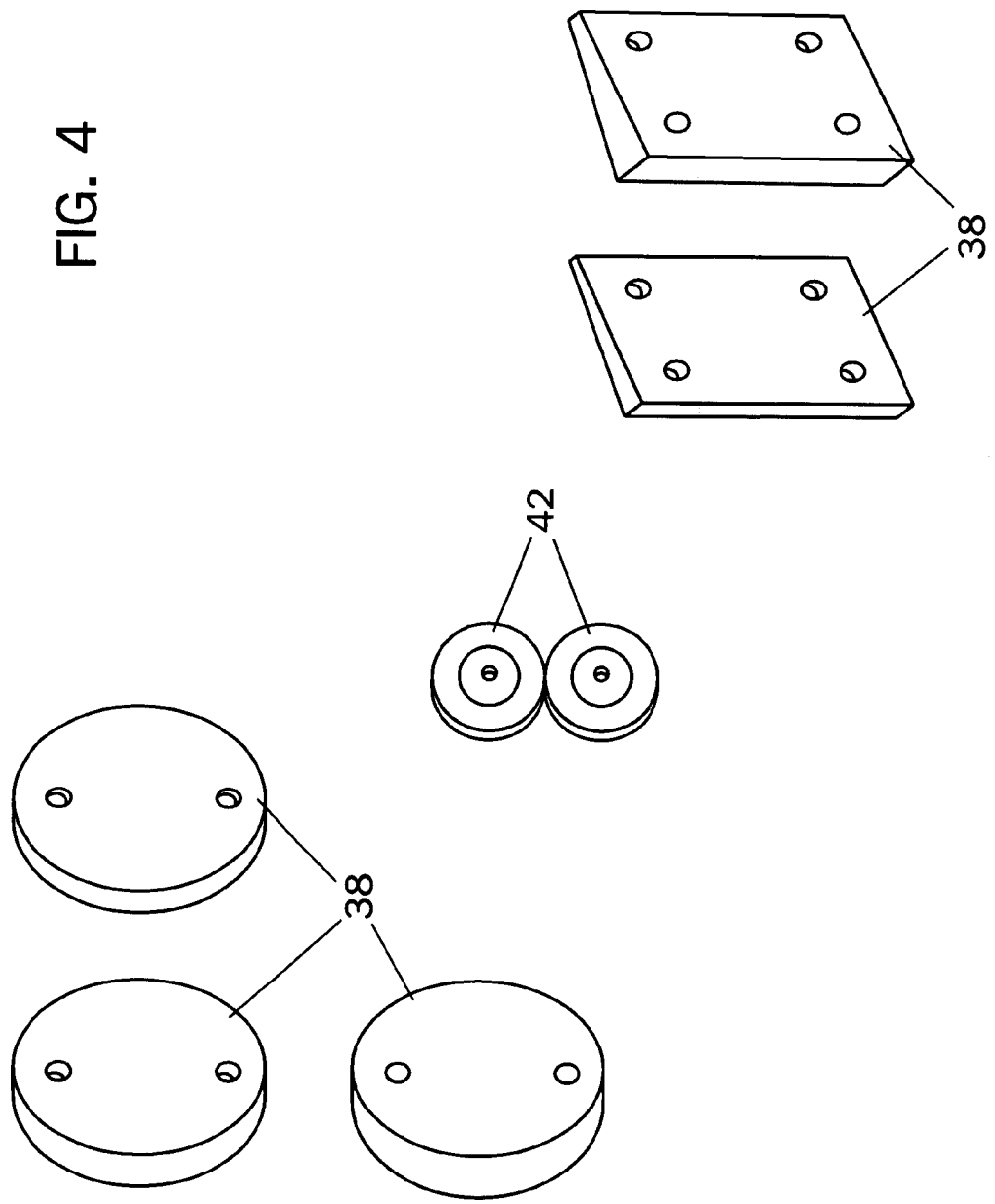

LIGHTING SYSTEM, POINT SOURCE LIGHTS THEREFOR AND METHODS OF MAKING THE SAME

RELATED APPLICATION DATA

This application is a continuation of Applicants' application Ser. No. 11/205,683, filed on 17 Aug. 2005, now U.S. Pat. No. 7,291,852 issued on 6 Nov. 2007.

BACKGROUND OF THE INVENTION

1. Field of the Invention

This invention relates to an ultraviolet fishing lighting system for fishing at night enabling the fisherperson to observe the movement of a fluorescent fishing line when a fish is biting at the lure.

2. Prior Art Statement

In the practice of sport fishing, especially bass tournaments, it is customary for the fisherperson to observe the line for movement to indicate when a fish has first taken the bait. Professional fisherpersons observe the line just prior to the point at which the line enters the water and the line as it lays upon the surface of the water. The recreational sport fisherperson usually observes the line at the end of the pole or between the end of the pole and the water. Observation of the line is relatively easy during daytime hours, however, the night fisherperson must rely upon fluorescent line and an ultraviolet light, commonly called a black light, which illuminates the fluorescent line. The market has a number of ultraviolet light units which may be attached to the gunwale of a boat using suction cups or the like. The size, mounting and configuration of these ultraviolet light units impedes the practice of sport fishing as the units are generally in the line of casting and are subject to being dislodged from the gunwale of the boat and thus lost. Furthermore, the ultraviolet light emanating from these units casts a pall over the entire area of the chosen fishing spot often also shining directly into the eyes of the fisherperson. Therefore, there is a great need to improve the "black light" commonly used by night fisherpersons by eliminating the "pall", directing the light toward the objects to be observed and readily and/or securely mounting the light.

It is known to provide a fishing lighting system comprising at least one lighting assembly which comprises at least one ultraviolet light source, at least one white light source and a means for separately controlling the light sources and a mounting base, the mounting base carrying the light sources and the means for separately controlling wherein the fishing lighting system is integral with a portion of the gunwale of a boat. For instance, see the U.S. Pat. No. 6,474,851 B1 issued on Nov. 5, 2002, to David Baley. The Baley lighting system has been found to be useful for the purposes claimed therein, however, it has also found that the white light is unnecessary, the base occupies a significant length of the gunwale or gunwale rub strip and is therefore subject to damage during docking and finally, the UV light source is diffuse and thus not properly directed. Therefore, there is a great need for a concentrated UV light source that is directed toward region of usage, has sufficient intensity at least 40 feet and is readily protected from the environment.

It is also known to provide a fluorescent fishing light mounted to a gunwale of a boat by suction cups. For instance, see the U.S. Design Pat. 299,550 issued on Jan. 24, 1989 to Duncan M. Payne. A separate shield mounted to the top of the light is now required to keep the light from shining in the face of fisherpersons using this light. This diffuse, undirected, scattered light casts a general pall about the entire environment making viewing of the fishing line strained. The general pall also attracts bugs to the light. There is a need for a focused UV light source which has sufficient intensity to enhance viewing of the fishing line, is directed toward the region of usage, can easily be substantially permanently mounted to the boat, protected from the environment and which diminishes attraction of bugs.

It is further known to provide a lighting strip mounted in the bumper guard for the boat to provide for the ship's directional lighting. For instance, see U.S. Pat. No. 5,495,401 issued on Feb. 27, 1996 to Graham P. Evans. These strips require 250 volts AC power normally not available on a fishing boat thus requiring a separate power source. Additionally, the lighting strip cannot be used for fishing as the light does not project far from the bumper guard but is merely observed to be present when viewed. Thus, there is a need for a fishing lighting system using electrical power available on a small fishing boat which may also function as a lighting strip for identification.

It is further known to provide a cargo vehicle perimeter clearance lighting system including an elongated core light conducting strip clad about its cross section with a translucent material layer having an index of refraction different from that of the core material to produce a light guide. The lighting strip is illuminated by a light source having light focusing reflectors to end-illuminate the light guide. For instance, see the U.S. Pat. No. 4,947,293 issued on Aug. 7, 1990 to Johnson, et al. It has been found by the inventors of the instant application that use of ultraviolet light for the light source does not radiate ultraviolet light from the translucent material of the Johnson, et al. patent and therefore there is a need for an ultraviolet lighting system that radiates light in a specific direction, has sufficient intensity to illuminate a desired region, can be readily mounted and protected from the environment.

William L. Hassler, Jr., in his U.S. Pat. No. 4,954,931 issued 4 Sep. 1990 claims a light source for producing a relatively uniform dispersed light emission along a length of a light bar, the bar comprising a prism made of polycarbonate having one frosted face and having a Light Emitting Diode lighting source in at least one end thereof. The light bar is illuminated but does not transmit light away from the light bar. Furthermore, it is been found by the inventors of the instant application that the ultraviolet inhibitors in the polycarbonate bar blocks ultraviolet light from passing from the polycarbonate prism of the Hassler, Jr., patent. Therefore, there is a need for an ultraviolet light source which may be readily placed upon, or secured to, a fishing vessel wherein the ultraviolet light source projects a directed ultraviolet light outwardly from the fishing vessel.

It is also known to provide a boat light system comprising a housing having top and bottom ends with a pair of elongate light sources mounted in the housing electrically connected to a plug at the lower end of the housing wherein a first light source emits black fluorescent light and the second light source emits a white fluorescent light, the housing mounted on the centerline of the boat at the front and/or the rear of the boat. For instance, see the U.S. Pat. No. 6,174,078, issued on 16 Jan. 2001 to Ohm, et al. The fluorescent lights, so mounted, interfere with the normal navigational lights of the boat and the black light is a source of irritation to the fisherperson while fishing. Therefore, there is a great need for a UV light source that projects a directed UV light outwardly from the side edge of the fishing vessel that protects the fisherperson from the UV light rays.

Furthermore, it is known to provide ultraviolet lamps on a head strap for night viewing of fluorescing objects including, but not limited to, monofilament fishing line, tattoos, invisible ink, golf balls and scorpions. For instance, see the LED Ultraviolet Headlamps available from Black Light World, P.O. Box 26, Cub Run, Ky. 42729 or the UV LED Blacklight Headlight with Adjustable Elastic Band for Scorpion Detecting available from Erin Sheffo, 3912 Nantasket St. Pittsburgh, Pa., 15207. The ultraviolet head lamps available are good for close-in viewing of luminescing objects but the luminescent strength is insufficient for professional night fishing. Additionally, these ultraviolet head lamps seem to cast a general pall over areas remote from the immediate vicinity of the lamp thus limiting the effectiveness thereof. Thus, the need for an ultraviolet light source which is directed outwardly from the fishing vessel is still needed.

Finally, it is known to provide a gazing point illuminating device comprising an LED panel including one or a plurality of LEDs attached to goggles or eyeglasses wherein an LED panel is placed at each of the left and an right end of the goggles or eyeglasses. For instance, see the U.S. Pat. No. 6,554,444 B2 issued on 29 Apr. 2003 to Shimada, et al. The focal distance and light intensity of the LEDs may be varied, however, the eyeglasses or goggles have driving motors to adjust to the focus of the light sources dependent upon the gaze of the wearer. The gazing point illuminating device is primarily used for medical operations, however, ostensibly could be used for observing a floating bobber in a fishing environment. Still, ultraviolet LED's are added to the white light LED's which defeats the purpose of the UVLED. Furthermore, the cost of such a device would be prohibitive for most fisherpersons and the goggles or glasses would still subject to being lost. Therefore, there is still a great need for an ultraviolet light source which may be readily placed upon, or secured to, a fishing vessel wherein the ultraviolet light source projects a directed the ultraviolet light outwardly from the fishing vessel and wherein the ultraviolet light source is protected from the environment.

SUMMARY OF THE INVENTION

Commonly used night fishing lighting systems heretofore have been portable bulky devices attached to the gunwale of a boat with suction cups and hence were subject to being lost as they are readily removed from the gunwale. Furthermore, these commonly used fishing lighting systems cast a general pall of blue light over the area of observation which has led to eye fatigue. A prior art device having white light LED's outboard of the eye pieces of eyeglasses or goggles has been proposed, however, as herein before stated the cost of such eyeglasses or goggles is prohibitive for most fisherpersons and the goggles are also subject to loss. In one night fishing lighting system, white light and ultraviolet light fluorescent bulbs are mounted on a housing made integral with the rub strip of the fishing boat, however, the use of fluorescent bulbs still cast a general pall over the entire area of observation, and, in general, the white light has been found be unnecessary. Therefore, it is an object of this invention to provide a lighting assembly for a fishing lighting system which comprises at least one ultraviolet light source, means for separately controlling the ultraviolet light source and a mounting base wherein the mounting base carries the ultraviolet light source and may additionally carry the means for separately controlling and wherein the fishing lighting system is mounted upon a portion of the side of a boat, the ultraviolet light source comprising an array of point source lights.

One significant feature of this invention is to provide a fishing lighting assembly for a fishing lighting system which comprises at least one ultraviolet light source mounted to a mounting base wherein a means for controlling the ultraviolet source is remote from the mounting base and wherein the fishing lighting system is adapted to be mounted upon a portion of the gunwale of a boat, the ultraviolet light source comprising an array of point source lights.

Yet another object of this invention is to provide a lighting assembly comprising a plurality of point source lights in an array wherein the point source lights are arranged in a substantially horizontal plane upon a mounting base, the point source lights spaced apart at intervals up to about 2 feet.

One goal of this invention is to a provide lighting assembly comprising a plurality of point source lights arranged in a substantially horizontal plane upon a mounting base wherein the point source lights have a wide viewing angle, preferably at least 45 degrees. Preferably though, the point source lights are spaced apart at intervals from about ½ inch to about two feet and have a narrow viewing angle between about five degrees to about 45 degrees.

One purpose of this invention is to provide a lighting assembly comprising a plurality of point source lights arranged in a substantially horizontal plane upon a mounting base, the point source lights preferably having a wide viewing angle and wherein light emanating from one point source light overlaps light emanating from an adjacent point source light.

A significant aim of this invention is to provide a lighting assembly comprising a plurality of point source light which are selected from the group comprising incandescent bulbs, high intensity bulbs and light emitting diodes.

Another object of this invention is to provide a fishing lighting assembly comprising a plurality of point source lights arranged in a substantially horizontal plane upon a mounting base, wherein light emanating from one point source light overlaps light emanating from an adjacent point source light at a specified distance from the mounting base.

Another goal of this invention is to provide a fishing lighting assembly comprising a plurality of point source lights arranged in an array upon a mounting base wherein light from each of the array of point source lights is projected into a series of adjacent to overlapping circles at a specified distance from mounting base wherein the point source lights are selected from the group comprising incandescent bulbs, high intensity bulbs and light emitting diodes.

And other purpose of this invention is to provide an ultraviolet lighting array which comprises a plurality of ultraviolet light emitting diodes arranged in a pattern wherein the lighting array casts a plurality of lighting cones in a generally outward direction for observation of the movement of a fluorescent line of a fishing system.

At least one another object of this invention is to provide a lighting assembly for a fishing lighting system comprising a base, at least one ultraviolet light emitting diode (UVLED) mounted on the base wherein the base has an integrated circuit and an electrical power source associated with the base and a cover protecting the UVLED, the integrated circuit and the power source.

BRIEF DESCRIPTION OF THE DRAWINGS

FIG. 4 is a perspective view of tapered mounting plates for aiming the lighting assembly of this invention.

DESCRIPTION OF THE PREFERRED EMBODIMENTS

While the various features of this invention are hereinafter described and illustrated as a an ultraviolet lighting array comprising a plurality of ultraviolet point light sources arranged in a pattern wherein the lighting array casts a plurality of lighting cones in a generally outward direction for observation of the movement of a fluorescent line of a fishing system, it is to be understood that the various features of this invention can be used singly or in various combinations thereof for a lighting assembly especially for a lighting system as can hereinafter be appreciated from a reading of the following description.

Figure 1:
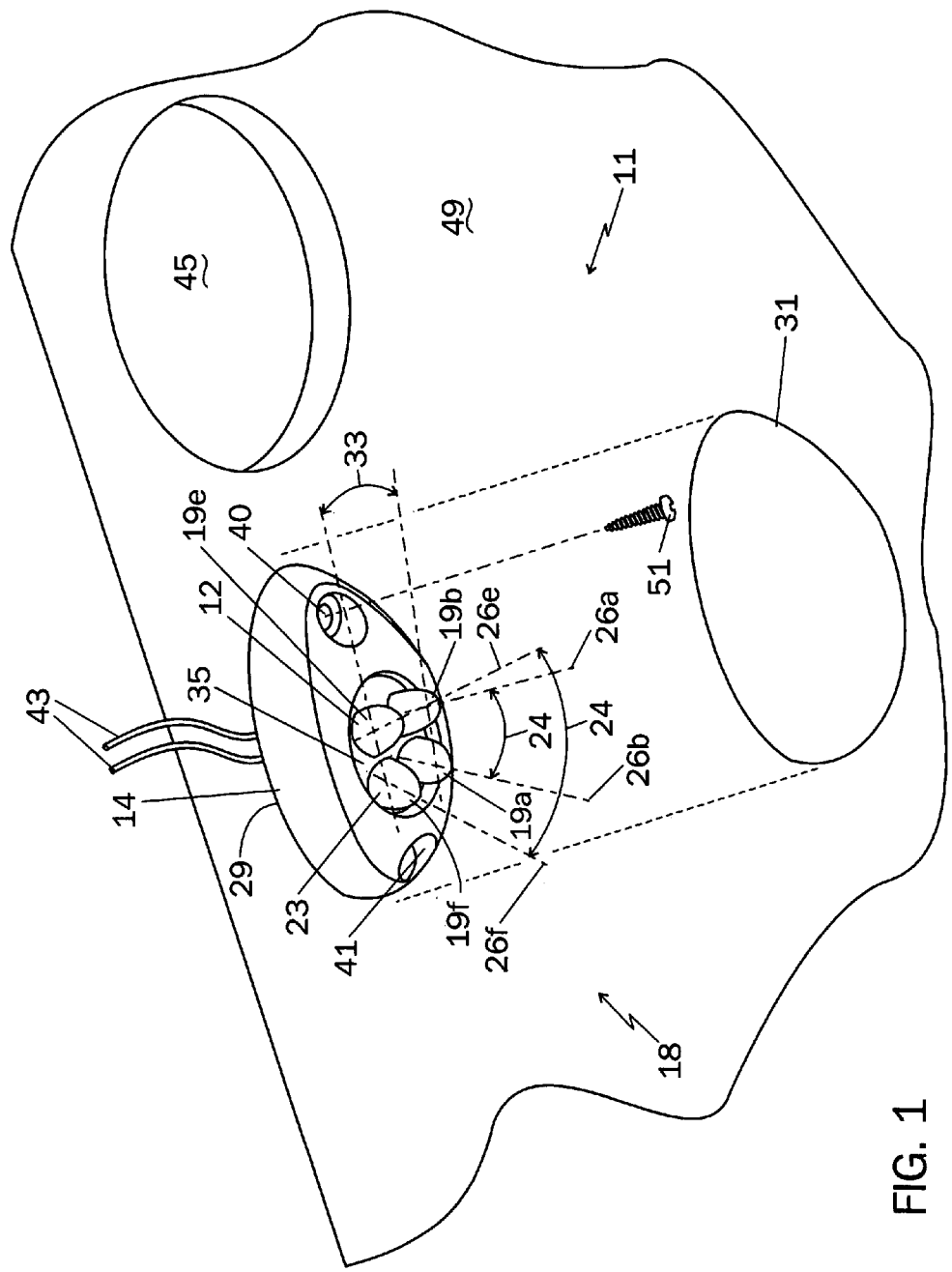
FIG. 1 is an enlarged perspective view of an alternate embodiment of the lighting assembly of this invention shown mounted upon a generally vertical surface of the side edge of a boat such as the side wall above, within or below the rub strip on the gunwale or on a vertical deck support of a pontoon boat.
Figure 2:
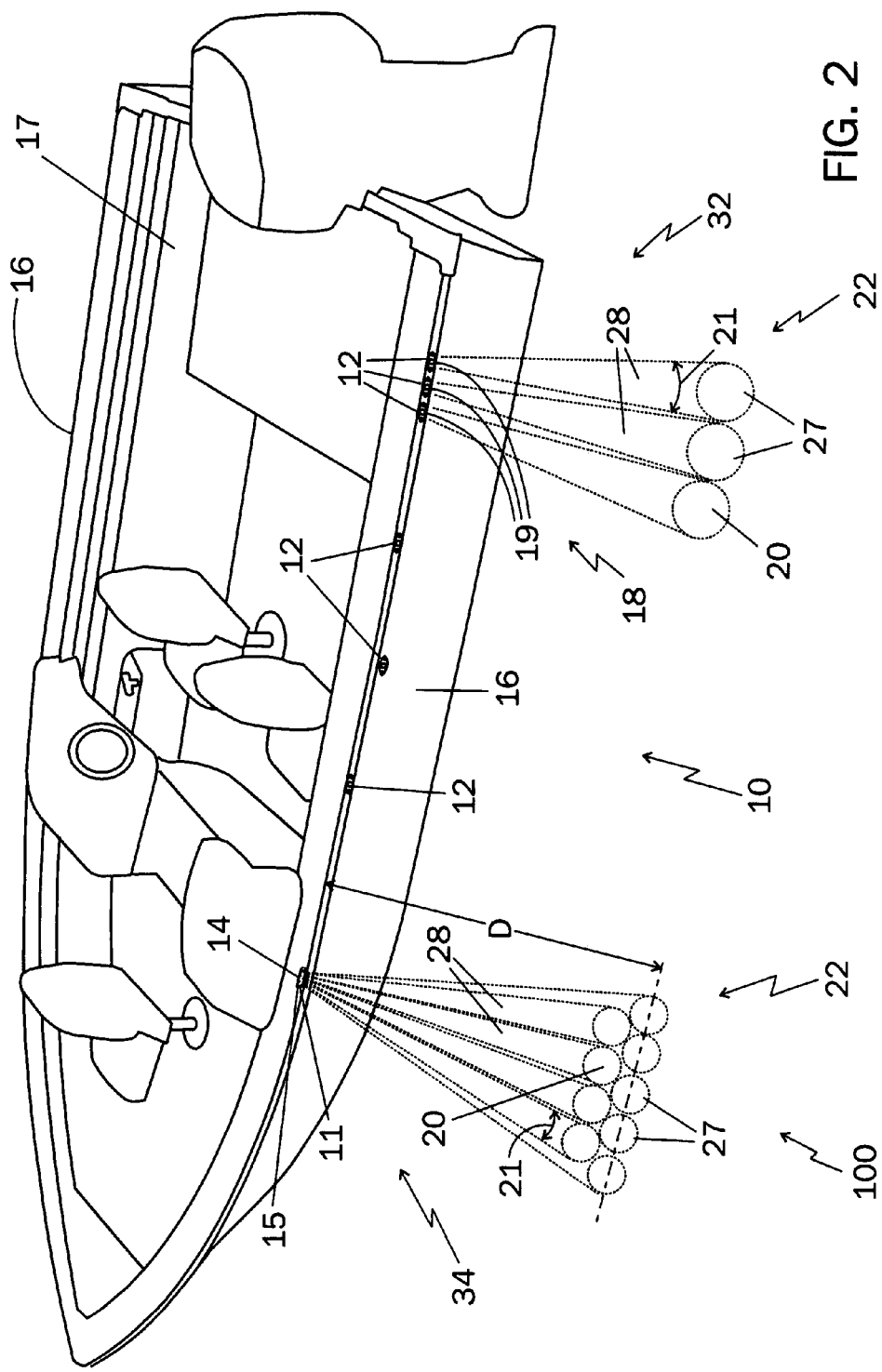
FIG. 2 is a perspective view of a boat having at least one embodiment of the lighting assembly mounted thereupon showing light emanating from the lighting assembly for use in night fishing.
Figure 3:
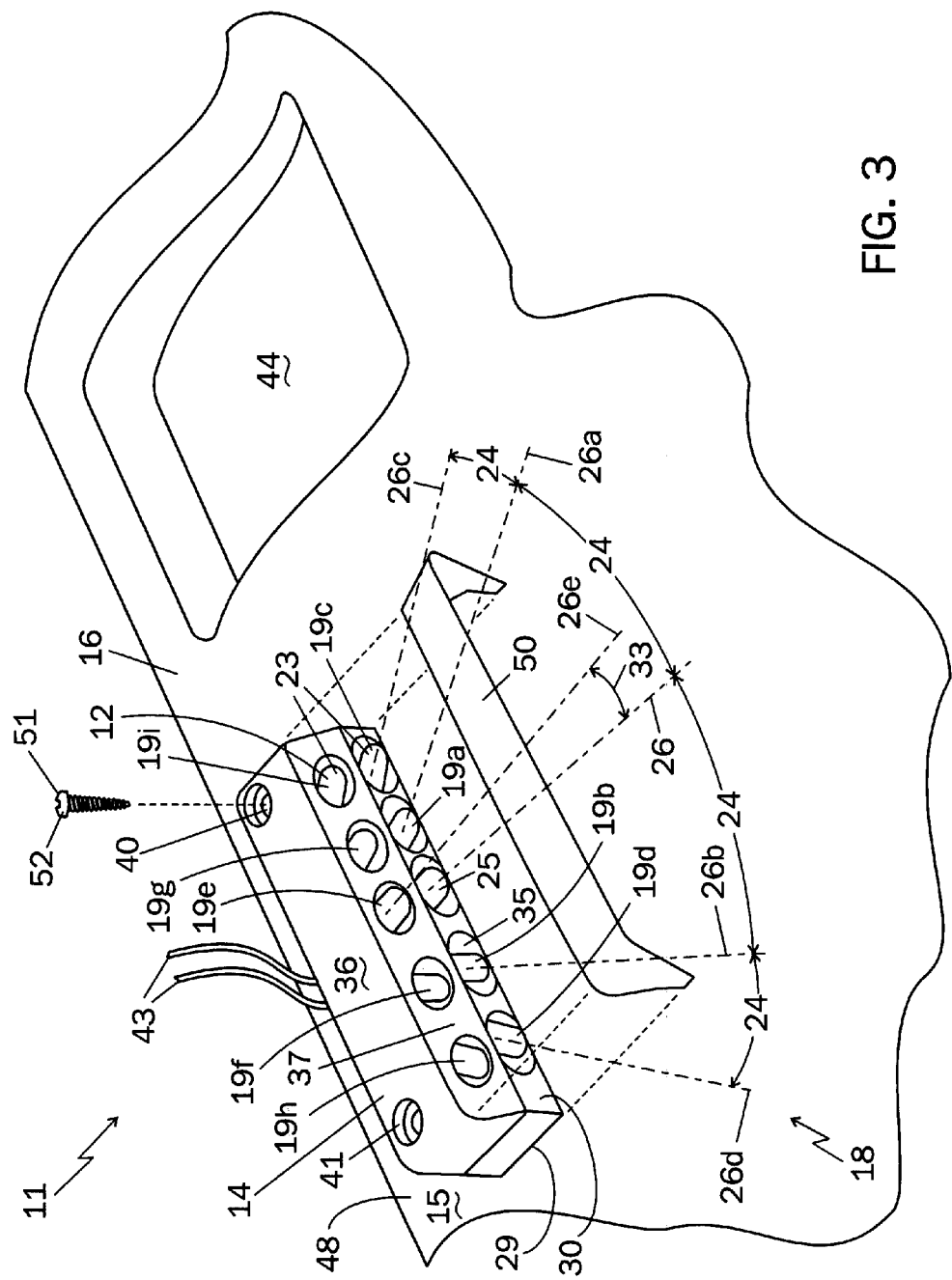
FIG. 3 is an enlarged perspective view of the preferred embodiment of the lighting assembly of this invention shown mounted upon a generally horizontal surface of the boat such as the top of the gunwale.

Referring now to the Figures, a lighting system 10 such as a fishing lighting system 100 shown in FIG. 2, lighting system 10 comprising at least one lighting assembly 11 of FIGS. 1 and 3, wherein lighting assembly 11 comprises at least one ultraviolet light source 12 carried in a mounting base 14, fishing lighting system 100 preferably mounted upon a portion 15 of the side 16 of a boat 17 wherein ultraviolet light source 12 comprises an array 18 of point source lights 19. Preferably, a plurality of point source lights 19 of array 18 are arranged within mounting base 14 having the central axes 26 of a some of the point source lights 19 arranged on a substantially horizontal plane and additional point source lights 19 arranged on a plane inclined from the horizontal plane. Lighting system 10 may further comprise a plurality of lighting assemblies 11 spaced apart at intervals of at least 2 inches, however, alternate arrangements have been found by the instant inventors to be beneficial for fishing, decorative purposes or identification.

According to the teachings of this invention, point source lights 19 were selected with wavelengths spanning the region from inside the visible spectrum into the ultraviolet region. Twenty-three point source lights 19 were individually lighted to determine a distance D from the location of the point source light 19 which would allow for observation of a 6 pound test fluorescent fishing line. Generally, point source lights 19 having shorter peak wavelengths provided visibility at greater distances, however, point source lights 19 were selected throughout the range of wavelengths from 390 nm to 408 nm for a direct comparison with a conventional "black light." The conventional "black light" comprises an ultraviolet fluorescent tube carried in a housing, the conventional "black light" fully described in the aforementioned U.S. Design Pat. 299, 550 issued on Jan. 24, 1989 to Duncan M. Payne.

Initially, linear arrays 18 of five point source lights 19 of each of five different wavelengths for a total of 25 point source lights, were arranged in separate parallel planes, point source lights 19 of each linear array 18 spaced at intervals of ½ in. upon a circuit board, point source lights 19 having axes 26-26d thereof lying parallel to each other upon the substantially horizontal plane. By switching between the conventional "black light" and each of the linear arrays 18, it was found that point source lights 19 having a viewing angle 21 of 30 degrees and a dominant wavelength of 395 nm provided the best visibility of a fluorescent line at fifty (50) feet for point source lights 19 at the edge of the visible spectrum. The conventional "black light," although casting a general pall over the entire viewing range, still appeared to have a wider field of vision. Thus, it was determined that point source lights 19 should be angled relative to one another and/or spaced at greater distances to achieve the wider field of vision provided by the conventional "black light."

In a second experimental apparatus, generally shown in FIG. 3 and now comprising a preferred embodiment, one point source light 19, centrally disposed on the horizontal plane within mounting base 14 and now designated central light 25, was arranged with axis 26 generally parallel to mounting surface 29 of mounting base 14. Point source lights 19a, 19b on the horizontal plane immediately adjacent to central light 25 had respective axes 26a, 26b disposed at angle 24 away from axis 26 of central light 25 by about 30 degrees. Thus, three point source lights 19 were arranged upon a circuit board within mounting base 14 producing a 90 degree field of vision, however, it was determined that additional point source lights 19 outboard of the initial three point source lights 19, 19a, 19b would provide for a substantially 150 degree field of visibility by angling the axes 26 of the outboard point source lights 19c, 19d at an angle of 60 degrees from axis 26 of central light 25. Therefore, the outboard point source lights 19c, 19d were canted at angle 24 of 30 degrees from the next inboard point source light 19a, 19c respectively. In this second apparatus, it was determined that point source light 19-19d having viewing angle 21 of 30 degrees, peak wavelength of 405 nm and a dominant wavelength of 395 nm provided the best visibility of a fluorescent line at specified distance D feet while providing a much darker overall environment. It was also determined that the preferred point source light 19 did not attract bugs to lighting assembly 11 nor when coupled with at least one other lighting assembly 11 to comprise lighting system 10.

Linear array 18 of point source lights 19 of the preferred embodiment identified just above as shown in FIG. 3, produced a band of light 22 shown at the aft location 32 of boat 17, band of light 22 comprising a plurality of substantially tangent areas 27 at specified distance D, however, it was again determined by the teachings of this invention that in order to satisfy the recreational fisherperson and to allow for rolling and pitching of a boat, band of light 22 would need to encompass a larger vertical field of vision above the water surface. Therefore, as further shown in FIG. 3, additional point source lights 19e-19i, were arranged within mounting base 14 with axes 26e-26i disposed at an angle 33 upwards from the substantially horizontal plane, angle 33 in the range from of up to about 60 degrees. When angle 33 is preferably about 15 degrees, cone 28 of light source 12 from point source light 19e overlaps cones 28 of light 20 from central light 25 and point source light 19b generally as shown at the forward location 34 of boat 17 in FIG. 2. It should be fully understood here that cones 28 of light sources 12 of additional point source lights 19-19i overlap immediately adjacent cones 28 of light sources 12 of point source lights 19-19d. Therefore, the intensity of light 20 from light source 12 at distance D generally outwardly along the horizontal plane from mounting base 14, effectively the same as the distance from the fisherperson observer, is augmented by point source lights 19e-19i arranged on the plane inclined above the substantially horizontal plane. Though the lighting assemblies 11 of this invention generally comprise at least one up to about ten point source lights 19, additional point source lights 19 may be provided in array 18 without departing from the scope of this invention. It has also been found by the teachings of this invention that when point source lights 19 having different intensities are used together, only the point source light 19 having the highest intensity illuminates the line and therefore, it is important to ensure that point source lights 19 are matched in intensity as well as wavelength.

Preferably, point source lights 19 of fishing lighting system 10 have a wide viewing angle 21 of at least 45 degrees wherein wide viewing angle 21 is defined as an included angle centrally disposed around point source lights 19. Thus, light 20 emanating from one point source light 19 overlaps light 20 emanating from an adjacent point source light 19 such that the object to be lighted, such as a fishing line, may be observed over a complete range of vision of the observer. Thus, a fluorescent line cast by a fisherperson may readily be observed for movement especially at or near the water line at a distance D when bait on the end of the line is first taken by a fish.

Point source lights 19 may be selected from the group comprising incandescent bulbs, high intensity bulbs and light emitting diodes, but preferably are light emitting diodes 23 having light 20 emitted at a wavelength between 300 and 450 nm, an apparent luminescence of at least forty (40) millicandela, (mcd) and a viewing angle of up to sixty (60) degrees. In the preferred embodiment, light 20 is emitted from light emitting diodes 23 at a peak wavelength of 405 nm, just inside the visible region of 390 to 770 nm with light on either side of the peak wavelength extending into the ultraviolet region down to about 380 nm. The dominant wavelength in the preferred light emitting diode 23 is 395 nm, the preferred viewing angle is 30 degrees and the apparent luminescence is 40 mcd (approximately 0.059 milliwatts per steradian). Table 1 shows engineering data for the various LED's tested in the second experimental apparatus described above, with the fifth column containing the preferred point source light 19 for light spanning the range from UV to just inside the visible spectrum.

In the preferred embodiment of FIG. 3, point source lights 19 are disposed at angles 24 relative to a centrally disposed point source light 19, here identified as central light 25. Angle 24 between central light 25 and an adjacent point source light 19 is up to 45 degrees, however, may be greater than 45 degrees where luminescence of point source light 19 is exceedingly great. Preferably, angle 24 is about equal to viewing angle 21 of point source light 19. Angle 24 may also be varied where viewing angle 21 is greater than 30 degrees and/or the preferred spacing specified below is exceeded. Where more than two point source lights 19 are mounted upon mounting base 14, angle 24 between point source light 19 adjacent central light 25 and another outboard adjacent point source light 19 is up to about 45 degrees, however, again angle 24 may be greater than 45 degrees as specified above. Thus, by arranging point source lights 19 close together as in the preferred embodiment, angle 24 is preferably 30 degrees making lighting cones 28 adjacent. It has been found by the teachings of this invention that point source lights 19 are best utilized when closely packed and arranged on different planes. Fishing lighting system 10 then generally comprises a plurality of lighting assemblies 11 spaced apart at intervals of at least two inches and more particularly, when lighting assemblies 11 are spaced at an intervals of about six feet.

In the preferred embodiment of FIG. 3, point source lights 19 have a narrow viewing angle 21 of less than 45 degrees, generally being of up to about 45 degrees wherein light 20 emanating from one point source light 19 overlaps light 20 emanating from an adjacent point source light 19 at specified distance D from mounting base 14. When so arranged, light 20 from array 18 of point source lights 19-19*d* is projected into a series of adjacent to overlapping areas 27 at specified distance D from mounting base 14 thus providing the observer with a relatively complete viewing of the object to be viewed. In addition, point source lights 19 may be arranged in other configurations, one configuration found to be particularly beneficial by the teachings of this invention has at least one point source light 19*e*-19*i* disposed at an angle 24 relative to central light 25 and at angle 33 relative to the substantially horizontal plane thus providing at least one adjacent overlapping area 27 spaced above or below the substantially horizontal plane thus providing a more complete viewing by the viewer. In this embodiment, angle 24 of at least of one point source lights 19*e*-19*i* is arranged with its axis 26 out of the horizontal plane of up to 45 degrees. In the preferred embodiment of FIG. 3, there are generally five point source lights 19-19*d* on the substantially horizontal plane and five point source lights 19*e*-19*i* on the plane inclined above the horizontal plane, all point source lights 19-19*i* mounted within mounting base 14. Mounting base 14 has point source light receiving holes 35 disposed in a frontal surface 30 thereof, frontal surface 30 generally perpendicular to mounting surface 29. Point source lights 19-19*i* are fitted within point source light receiving holes 35 and may protrude slightly therefrom. Preferably, mounting base 14 has a hood 50 extending from the upper surface 36 thereof, hood 50 shielding the observer from the ultraviolet light emanating from point light sources 19-19*i*. Mounting base 14 may further have an inclined portion 37 of frontal surface 30 wherein inclined surface 37 is perpendicular to the plane inclined from the horizontal plane. As the inclined plane may be up to 45 degrees from the substantially horizontal plane, portion 37 may be thus be used as an visual indication of the amount of angular displacement of the inclined plane from the horizontal plane, it being fully understood here that portion 37 may be inclined at any angle up to 45 degrees. Mounting base 14 is most preferably mounted to upper surface 48 of the gunwale of boat 17 by mounting screws 51 passing through screw holes 40, screw holes 40 having a recess 41 therein for receiving and recessing the head 52 of the screw 51 below top surface 36 of mounting base 14. Although screws are the preferred means of mounting, other mounting structures may be used to advantage. For instance, mounting base 14 may be provided with an adhesive mount on mounting surface 29 or screws 51 may be screwed into suction cups 42 found in FIG. 4. In addition, as few boats 17 have upper surface 48 of the gunwale parallel to the surface of the water, at least one tapered base 38 may be employed to provide light from point source lights 19-19*d* on a plane substantially parallel to the surface of the water by raising one edge of mounting base 14 relative to upper surface 48 of the gunwale of boat 17. Preferably, a plurality of tapered bases 38 of differing thickness are provided with mounting base 14 for leveling. It may be necessary to use more than one tapered base 38 in order to achieve the proper alignment of light from point light sources 19-19*i*. As mounting base 14 may be removably mounted to upper surface 48 of the gunwale, lighting assembly 11 is thus portable and may be moved from one location to another. Furthermore, it is within the scope of this invention to mount at least one lighting assembly 11 on a separate, movable structure, such as a tackle box wherein the lighting system 10 thus produced is readily portable. Of course, it is also within the scope of this invention to provide a depressed area 44 in upper surface 48 of the gunwale of boat 17 wherein lighting assembly 10 is mounted therein, depressed area 44 preferably produced at the production of boat 17.

Referring now to the alternate embodiment of FIG. 1, LEDs 19a and 19b are arranged in a straight line on the horizontal plane having the central axes 26 thereof angled outwardly by angle 24, light from LEDs 19a and 19b projecting light substantially outwardly along the horizontal plane while point light sources 19e and 19f are mounted within base 14 at angle 33 relative to LEDs 19a and 19b. As herein before described, point light sources 19a, 19b are disposed at an angle of approximately 30 degrees relative to each other and point light sources 19e, 19f are arranged at an angle of up to about 30 degrees upwardly relative to the horizontal plane described by point light sources 19a, 19b. Base 14 also preferably has wedge shape elements 38 of FIG. 4 for engagement with mounting surface 29 of lighting assemblies 11 for aiming of light 20 from ultraviolet light sources 12 emanating from lighting assemblies 11 in the desired direction generally parallel to the surface of the water. In this alternate embodiment, lighting assembly 11 for fishing lighting array 18 comprises an oval base 14 with at least one ultraviolet light emitting diode 23 (UVLED) mounted in mounting base 14 generally as shown in FIG. 1. Base 14 may further comprise an integrated circuit board and an electrical power connection associated with base 14, lighting assembly 11 also preferably having a cover 31 protecting UVLED 23 and the integrated circuit and power connection if included. Preferably, however, lighting assembly 11 comprises only point light sources 19a, 19b, 19e and 19f mounted in mounting base 14 with electrical leads 43 extending therefrom. Lighting assembly 11 of this alternate embodiment may be mounted on side 16 of boat 17 either above, below or within the rub strip of the gunwale and coupled with other similar lighting assemblies 11 in array 18 along side 16. As hereinbefore stated, lighting assemblies 11 may be placed at intervals along side 16 to achieve the desired amount of UV light at distance D from lighting assembly 11. In fact, it has been found most beneficial to mount one lighting assembly 11 of this alternate embodiment on side 16 below the rub strip at each fishing location and at least one other lighting assembly 11 below the rub strip between the forward and aft fishing locations. Since lighting assemblies 11 are below the rub strip, it is usually unnecessary to provide a hood 50 over lighting assemblies 11, however, certain rub strip configurations may require mounting lighting assemblies 11 above the rub strip. When necessary to mount above the rub strip, cover 31 may be used over lighting assemblies 11 wherein a portion of cover 31 is made opaque to shield the observer's eyes from the UV light. Mounting surface 29 of lighting assembly 11 of this alternate embodiment is generally perpendicular to the plane described by light 20 from point light sources 19a and 19b and thus can be mounted directly to a vertical surface 49 such as an upright deck support of a pontoon boat or side 16 of boat 17. Oval tapered bases 38 are provided to aim light 20 from ultraviolet light sources 12 generally parallel to the surface of the water where vertical surface 49 is not perpendicular to the surface of the water. Alternate lighting assemblies 11 may also be mounted directly to vertical surface 49 with screws 51, adhered to vertical surface 49 with an adhesive or removably affixed thereto with suction cups 42. Most preferably, alternate lighting assemblies 11 are mounted in a preformed recess 45 shown in FIG. 1 adjacent lighting assembly 11. Preformed recess 45 is preferably provide at the time of manufacture of boat 17.

As power on a fishing vessel is commonly 12 volts DC, the integrated circuit board is usually disposed remote from lighting assemblies 11 and carries resistors in series with each lighting assembly 11 in order to supply the proper forward voltage of 3.7 to 4.0 volts DC to the UVLEDs 23 of lighting assembly 11. Preferably, a means for controlling lighting assemblies 11 is also disposed remote from lighting assembly 11 for ready access by the fisherperson. Typically, UVLEDs 23 draw approximately 20 milliamps and therefore, for each UVLED 23, a resistance of 400 ohms is typically used, however, since the preferred lighting assemblies 11 of this invention comprise a cluster of UVLEDs 23 arranged in array 18, the resistor on the circuit board in sized according to the number of UVLEDs 23 in array 18. FIG. 1 shows a plurality of UVLEDs 23 arranged within mounting base 14, however, it is to be fully understood that a single UVLED 23 could comprise lighting assembly 11. The construction of printed circuit boards is widely known in the field and therefore description of the method of producing a circuit board, the method of surface mounting of UVLEDs 23, resistors and means for controlling need not be described herein.

Thus, it may be said that ultraviolet lighting array 18 comprises a plurality of ultraviolet light emitting diodes 23 arranged in a pattern, lighting array 18 casting a plurality of lighting cones 28 in a generally outward direction for observation of the movement of a fluorescent line of a fishing apparatus. Of course, lighting array 18 may be used for other purposes such as decorative lighting, identification lighting or mood lighting. It should also be understood that any fluorescing object within lighting cones 28 would be at least partially observed depending upon the distance the fluorescing object lies from the closest ultraviolet light source 12 of ultraviolet lighting array 18.

Another pattern for point light sources 19 is array 18 of lighting assemblies 11 arranged at intervals of about two feet along side 16 of a fishing vessel 17 each point light source 19 mounted within mounting base 14. Point source lights 19 may each be provided with the proper forward voltage of 3.7 to 4.0 Vdc, however, a plurality of lighting assemblies 11 may be fed from a single power source providing the forward voltage to the plurality of lighting assemblies 11. Point source lights 19 have a viewing angle 21 of up to 60 degrees, however, it has been found that to provide for overlapping areas 27 of light 20 from ultraviolet light sources 12 at a distance of 50 feet for point light sources 19 arranged at two foot intervals, viewing angle 21 is preferably less than 10 degrees and more specifically about 5 degrees. Arranging point light sources 19 at two foot intervals produces a narrow, but intense, field of vision at the specified distance of 50 feet, however, cones 28 of light 20 from ultraviolet light sources 12 are not adjacent and thus areas adjacent the fishing vessel 17 are not illuminated by light 20 from ultraviolet light sources 12. Furthermore, the field of vision is essentially limited to the length of the fishing vessel 17 plus the size of one area 27. Therefore, array 18 of point source lights 19 generally has point source lights 19 spaced at intervals of less than two feet, has point source lights 19 with a greater viewing angle 21 and has point source lights 19 outboard of central light 25 angled outwardly therefrom as recited in the preferred embodiment in order to increase the field of vision. Additional lighting assemblies 11 may then be placed along side 16 as desired by the observer.

In yet another embodiment, lighting assembly 11 may be mounted on an end of a flexible tube wherein the flexible tube may be wrapped around a cleat to direct light 20 from ultraviolet light source 12 outwardly from side 16. Alternately, the flexible tube could be centrally mounted at or near the fore and aft fishing locations wherein the flexible tube may be pointed outwardly from boat 17.

While the present invention has been described with reference to the above described preferred embodiments and alternate embodiments, it should be noted that various other embodiments and modifications may be made without departing from the spirit of the invention. Therefore, the embodiments described herein and the drawings appended hereto are merely illustrative of the features of the invention and should not be construed to be the only variants thereof nor limited thereto.

TABLE 1

| | | | | | | | |
|---|---|---|---|---|---|---|---|
| 5 MM | 5 MM | 5 MM | 5 MM | 5 MM | 5 MM | 5 MM | Diameter |
| | | InGaN | | InGaN | InGaN | InGaN | Material |
| VIOLET | UV DICE | PURPLE | UV | UV | UVC | VIOLET | Emitted Color |
| CLEAR | CLEAR | CLEAR | CLEAR | CLEAR | CLEAR | CLEAR | Lens Color |
| 20 ma | 20 ma | 20 ma | 30 ma | 20 ma | 30 ma | 20 ma | Forward current |
| | (−20/+75) C | (−40/+80) C | (−25/+85) c | (−25/+85) c | (−40/+85) c | (−40/+85) C | Operating Temp |
| | (−40/+100) C | | (−35/+100) C | (−40/+85) c | | (−40/+85) C | Storage Temp |
| | 260 c @ 5 sec | 260 c @ 5 sec | 260 c @ 5 sec | 260 c @ 5 sec | 260 c @ 5 sec | 260 c @ 5 sec | Soldering Temp |
| | | | 1000 v | | | | Electrostatic Disc |
| | | 170 mw | 120 mw | 80 mw | 100 mw | 80 mw | Power dissipation |
| | 120 ma | 100 ma | 100 ma | 100 ma | 100 ma | 100 ma | Peak Fwd Current |
| 5 v | 5 v | | 5 v | 5 v | 5 v | 5 v | Reverse voltage |
| | 3.5/4.0 | 3.4/3.6 | 3.7/4.0 | 3.6/4.5 | 3.8/4.2 | 3.5/4.0 | Forward voltage |
| | 500/800 mcd = .73-1.17 mw/sr | 150 mcd = 0.22 mw/sr | 10 mcd = 0.016 mw/sr | 40 mcd = 0.059 mw/sr | 140 mw/sr 95620 mcd (typ) | 50 mcd = .073 mw/sr | Luminescence |
| 30 d | 30 d | 25 d | 30 d | 30 d | 20 d | 30 d | Viewing angle |
| 390 nm | 400 nm | 402 nm | 395 nm | 405 nm | 400 nm | 395 nm | Peak wavelength |
| 405 nm | | | | 395 nm | 395 nm | | Dominant waveln |
| | | | 20 nm | 25 nm | | | Spectrum width |

We claim:

1. A lighting assembly for a lighting system, said lighting assembly comprising at least one ultraviolet light source, a mounting base and means for powering said at least one ultraviolet light source, said mounting base carrying said at least one ultraviolet light source, said lighting system mounted upon a portion of a side of a boat, said at least one ultraviolet light source comprising an array of point source lights arranged upon said mounting base in at least one linear array.

2. A lighting assembly as in claim 1 wherein said point source lights of said array are arranged in a substantially horizontal plane upon said mounting base.

3. A lighting assembly as in claim 2 wherein said point source lights are spaced apart at intervals up to about 2 feet.

4. A lighting assembly as in claim 3 wherein said point source lights have a wide viewing angle.

5. A lighting assembly as in claim 4 wherein said wide viewing angle is at least 45 degrees.

6. A lighting assembly as in claim 5 wherein light emanating from one said point source light overlaps light emanating from an adjacent said point source light.

7. A lighting assembly as in claim 6 wherein said point source lights are selected from the group comprising incandescent bulbs, high intensity bulbs and light emitting diodes.

8. A lighting assembly for a lighting system as in claim 1 wherein at least one said mounting base carrying said array of point source lights is mounted on a side of a fishing vessel below a rub strip at least one forward fishing location and at least one other mounting base carrying said array of point source lights is mounted on a side of a fishing vessel below a rub strip at least one aft fishing locations.

9. An ultraviolet lighting array comprises a plurality of ultraviolet light emitting diodes arranged in at least one linear pattern upon a base, said lighting array casting a plurality of lighting cones in a generally outward direction from said base for observation of the movement of a fluorescent line of a fishing system.

10. An ultraviolet lighting array as in claim 9 wherein said linear pattern comprises up to about ten point source lights.

11. An ultraviolet lighting array as in claim 10 wherein said point source lights are closely spaced upon said base.

12. An ultraviolet lighting array as in claim 9 wherein said base is placed upon a side portion of a fishing vessel.

13. An ultraviolet lighting array as in claim 9 wherein said base is secured to a portion of a gunwale of a boat.

14. An ultraviolet lighting array as in claim 13 wherein said base is secured to an edge of said gunwale.

15. An ultraviolet lighting array as in claim 14 wherein said base is mounted within a rub strip of said gunwale.

16. An ultraviolet lighting array as in claim 15 wherein said base comprises a rub strip of said gunwale.

17. A lighting assembly for a fishing lighting system comprising a base, at least one ultraviolet light emitting diode (UVLED), said at least one UVLED mounted on said base, said base having an integrated circuit and an electrical power source associated with said base, said lighting assembly having a cover protecting said UVLED, said one UVLED on said base spaced from at least one other adjacent UVLED on said base at intervals of up to about 2 feet.

18. An ultraviolet lighting array as in claim 17 wherein said one UVLED on said base is contiguous to at least one adjacent UVLED.

19. An ultraviolet lighting array as in claim 17 wherein said one UVLED and said at least one other UVLED project a band of ultraviolet light into tangent areas at specified distance from said base.

20. An ultraviolet lighting array as in claim 19 wherein said specified distance from said base is 50 feet.

* * * * *